(12) United States Patent
Berset et al.

(10) Patent No.: US 6,338,838 B1
(45) Date of Patent: Jan. 15, 2002

(54) PHOTOSTABLE COSMETIC LIGHT SCREENING COMPOSITIONS

(75) Inventors: Guy Berset, Onex; Gilbert Pittet, Coppet, both of (CH); Joël François Richard, Longué; Dominique Sidrac, Saint-Julien, both of (FR)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/567,652

(22) Filed: May 9, 2000

(30) Foreign Application Priority Data

May 12, 1999 (EP) .............................. 99109515

(51) Int. Cl.⁷ .......................... A61K 7/42; A61K 7/44; A61K 31/74; A61K 7/00
(52) U.S. Cl. ...................... 424/59; 424/60; 424/78.02; 424/78.08; 424/400; 424/401
(58) Field of Search ........................... 424/59, 60, 400, 424/401, 78.02, 78.08

(56) References Cited

U.S. PATENT DOCUMENTS

| | | | |
|---|---|---|---|
| 5,372,804 A | 12/1994 | Khoshdel et al. | 424/59 |
| 5,576,354 A | 11/1996 | Deflandre et al. | 514/685 |
| 5,876,699 A | 3/1999 | DiSomma et al. | 424/59 |
| 5,993,831 A | 11/1999 | Ribier et al. | 424/401 |

FOREIGN PATENT DOCUMENTS

| | | |
|---|---|---|
| DE | 43 36 407 | 4/1995 |
| EP | 0 514 491 B1 | 11/1993 |
| EP | 0 573 229 A2 | 12/1993 |
| EP | 0 610 026 A1 | 8/1994 |
| EP | 0 669 124 A1 | 8/1995 |
| EP | 0 780 119 A1 | 6/1996 |
| FR | 2 658 075 | 8/1991 |
| FR | 2 681 248 | 3/1993 |
| FR | 2 687 914 | 9/1993 |
| FR | 2 755 856 | 5/1998 |

*Primary Examiner*—Shelley A. Dodson
(74) *Attorney, Agent, or Firm*—Bryan Cave LLP

(57) ABSTRACT

The present invention relates to a photostable cosmetic or pharmaceutical light screening composition containing a dibenzoylmethane UV-A screening agent and a p-methoxycinnamate UV-B screening agent, one of said agents being incorporated into a polymer latex; and, optionally, other conventional UV-A and UV-B screening agents. Additionally, the present invention relates to a method of photostabilizing dibenzoyl-methane UV-A screening agents and p-methoxycinnamate UV-B screening agents when used together, by incorporating one of these agents into a polymer latex.

29 Claims, No Drawings

PHOTOSTABLE COSMETIC LIGHT SCREENING COMPOSITIONS

FIELD OF THE INVENTION

The invention relates to photostable cosmetic or pharmaceutical light screening compositions for the protection of the human epidermis or hair against ultraviolet rays of wavelengths between 280 and 400 nm (UV-A/UV-B).

More specifically, the invention relates to photostable light screening compositions containing a dibenzoylmethane UV-A screening agent and a p-methoxycinnamate UV-B screening agent wherein one of the screening agents is incorporated in a polymer latex.

BACKGROUND OF THE INVENTION

U.S. Pat. No. 5,372,804 (Chesebrough-Pond) relates to cosmetic compositions having at least one light screening agent wherein the light screening agent, is carried in or on polymer latex particles. The polymer latex particles effect a good deposition of the light screening agents onto hair or skin. Specifically disclosed light screening agents include benzophenone compounds, dibenzoylmethane derivatives and cinnamate derivatives, such as 2-ethylhexyl p-methoxycinnamate (PARSOL® MCX). The polymer particles employed may be of any polymeric material that is a good film former. The polymer particles may be substantially solid or may be porous and have a particle size of about 10–1000 nm. In order to get polymers having good film forming characteristics, a low glass transition temperature in the region of the temperature of normal use of the cosmetic composition, approximately 30° C., is required.

The above mentioned U.S. patent only discloses that light screening agents can be incorporated into a latex, thereby achieving the advantage of enhanced deposition. Said U.S. patent does not address the problem of photostability, which problem is due to an interaction of 4-tert. butyl-4'-methoxydibenzoyl-methane (PARSOL® 1789) with other light screening agents under light especially with 2-ethylhexyl p-methoxycinnamate (PARSOL® MCX).

Cosmetic light screening compositions based on dibenzoyl methane derivatives as UV-A screening agent and photostabilized with 3,3-diphenylacrylate derivatives are described in the European Patent Publication EP 0 514 491 B1 and in the European Publication EP 0 780 119 A1. However, this type of stabilization does not prevent the photochemical interaction between cinnamate derivatives, such as 2-ethylhexyl p-methoxycinnamate, and dibenzoyl-methane derivatives, such as 4-tert. butyl-4'-methoxydibenzoyl-methane.

SUMMARY OF THE INVENTION

It has now been found that the photostability of light screening compositions containing a dibenzoyl methane UV-A screening agent and a p-methoxycinnamate UV-B screening agent is improved if one of said light screening agents is incorporated into a polymer latex.

Accordingly, one aspect the invention is concerned with a method of photostabilizing mixtures of a dibenzoyl-methane UV-A screening agent and a p-methoxycinnamate UV-B screening agent in a light screening composition, which method comprises incorporating one of said light screening agents into a polymer latex.

In still another aspect the present invention is concerned with a light screening composition containing, based on the total weight of the composition, about 0.5 wt % to about 5 wt % of a dibenzoylmethane UV-A screening agent incorporated into a polymer latex, about 1 wt % to about 15 wt % of a p-methoxycinnamate UV-B screening agent; and, optionally, other conventional UV-A and UV-B screening agents.

In yet another aspect the present invention is concerned with a light screening composition containing, based on the total weight of the composition, about 1 wt % to about 15 wt % of p-methoxycinnamate UV-B screening agent incorporated into a polymer latex;

about 0.5 wt % to about 5 wt % of a dibenzoylmethane UV-A screening agent; and, optionally, other conventional UV-A and UV-B screening agents.

DETAILED DESCRIPTION OF THE INVENTION

As far as the dibenzoylmethane UV-A screening agent is concerned, the preferred compound is 4-tert. butyl-4'-methoxydibenzoyl-methane, which is sold under the tradename PARSOL® 1789.

Other suitable compounds of this particular type include: 2-methyldibenzoyl-methane, 4-methyldibenzoyl-methane, 4-isopropyldibenzoyl-methane, 4-tert. butyldibenzoyl-methane, 2,4-dimethyldibenzoyl-methane, 2,5-dimethyldibenzoyl-methane, 4,4'-diisopropyldibenzoyl-methane, 2-methyl-5-isopropyl-4'-methoxydibenzoyl-methane, 2-methyl-5-tert. butyl-4'-methoxydibenzoyl-methane, 2,4-dimethyl-4'-methoxydibenzoyl-methane, and 2,6-dimethyl-4-tert. butyl-4'-methoxydibenzoyl-methane.

As used herein the term "p-methoxycinnamate UV-B screening agent" refers to compounds such as 2-ethoxyethyl p-methoxycinnamate, 2-ethylhexyl (or pentyl) p-methoxycinnamate, potassium p-methoxycinnamate, sodium p-methoxycinnamate, ammonium p-methoxycinnamate, salts of primary, secondary or tertiary amines of p-methoxycinnamic acid like mono-, di-, tri-ethanol amine salt and the like. Preferred is 2-ethylhexyl p-methoxycinnamate, sold under the tradename PARSOL® MCX.

As used herein, the term "polymer latex" refers to a stable colloidal dispersion of polymer particles in an aqueous or an aqueous based phase including polymers and/or copolymers of unifunctional monomers and/or multifunctional monomers. The dibenzoylmethane UV-A screening agent or the p-methoxycinnamate UV-B screening agent is incorporated into the polymer latex.

As used herein the term "unifunctional monomers" includes $C_1$–$C_6$-alkyl (meth)acrylate, acrylic acid, methacrylic acid, styrene, ethylene, propylene, butylene, butadiene, isoprene, isobornyl methacrylate (IBOMA), trifluoroethyl methacrylate, perfluoralkyl 2-ethylacrylate and the like.

As used herein the term "multifunctional monomers" includes allyl methacrylate (ALMA), ethyleneglycol dimethacrylate (EGDMA) and the like.

A preferred polymer latex is a stable colloidal dispersion of copolymer particles of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA).

The polymer particles can have a matrix structure within which the dibenzoyl-methane UV-A screening agent or the p-methoxycinnamate UV-B screening agent is homogeneously distributed over the whole volume of the polymer particles, or the polymer particles can have a reservoir structure.

As used herein the term "reservoir structure" refers to particles having a polymer core surrounded by a polymer shell, wherein the core contains the dibenzoylmethane UV-A screening agent or the p-methoxycinnamate UV-B screening agent.

In one aspect, the core and the shell portions of the core/shell polymer particles may have the same chemical composition with regard to the monomers used. Suitable monomers used include unifunctional and multifunctional monomers as listed above.

In another aspect, the core and shell portions of the core/shell polymer particles may differ in their chemical composition. In this case, the monomers used in the core portion of the core/shell particles may also include the unifunctional and multifunctional monomers as listed above. The monomers used in the shell portion of the core/shell particles suitably include hydrophilic or fluorinated monomers.

Preferred core/shell particles include particles wherein
  a) the core consists of a polymer and/or a copolymer of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA); and
  b) the shell consists of hydrophilic polymer or fluorinated polymer chains.

Hydrophilic polymer shells are obtainable by copolymerization of monomers containing carboxylic acid groups such as acrylic acid, methacrylic acid, monomers bearing hydroxyl groups, such as, e.g., hydroxy-$C_1$–$C_6$-alkyl (meth)acrylate, (HEMA) and acrylamides (AAm). A suitable hydroxy-$C_1$–$C_6$-alkyl (meth)acrylate is hydroxyethyl methacrylate.

Fluorinated polymer shells are obtainable by copolymerization of acrylic esters, such as, e.g., methyl methacrylate (MMA) or isobornyl methacrylate (IBOMA) with fluorinated monomers, such as, e.g., trifluorethy methacrylate (TRIFEMA) or perfluoroalkyl 2-ethylacrylate (PF2EA).

The core can be surrounded by a single shell or by two or more shells, whereby the first shell surrounding the core and the following shell may be formed of the same polymer particles or of different polymer particles. For example, the first shell may be formed of a hydrophilic polymer and the following shell may be formed of a fluorinated polymer and vice versa.

If core and shell are not formed of the same polymer particles, a two component core-shell polymer is obtained having various morphological structures as described by Chen et al., Macromolecules 1991, 24, 3779–3787.

The polymer particles as defined above have a glass transition temperature between about 50° C. and about 100° C. The glass transition temperature can be adjusted to a given value by choosing the initial content of each monomer and by crosslinking with the above mentioned multifunctional monomers. Generally, a higher content of crosslinking agent increases the glass transition temperature, while increased alkyl chain lenghts in acrylate monomers result in lower glass transition temperatures of the polymer latex. Further, the glass transition temperature of the polymer latex will be lowered by increased levels of the incorporated screening agent, e.g., PARSOL® 1789.

The glass transition temperature of the polymer particles used for the core portion may be the same or different compared to the glass transition temperature of polymer particles used for the shell portion.

The polymer latex containing polymer particles having the dibenzoylmethane UV-A screening agent or the p-methoxycinnamate UV-B screening agent incorporated into the latex can be produced by emulsion polymerization including a crosslinking procedure. Thus, polymer particles having a glass transition temperature >50° C., preferably >70° C. are obtained.

The glass transition temperature is important since the polymer particles must be in a glassy state at storage temperature to impart a high stability and tightness to the system.

The preparation of latex polymers by emulsion polymerization has long been known. For example, U.S. Pat. No. 5,189,107 discloses that latex polymers having uniform particle size can be obtained by using latex seeds in the polymerization reaction to better control the particle size distribution.

Thus, the invention also comprises a process for the preparation of polymer particles having a matrix structure within which a dibenzoylmethane UV-A-screening agent or a p-methoxycinnamate UV-B screening agent is homogeneously distributed over the whole volume of the particles by
  a) dissolving the dibenzoylmethane UV-A screening agent or the p-methoxycinnamate UV-B screening agent in a blend of monomers;
  b) pre-emulsifying the solution of step a) in an aqueous solution containing an emulsifier;
  c1) continuously introducing the pre-emulsion of step b) into a reactor containing an aqueous initiator solution or
  c2) introducing a small amount of the pre-emulsion of step b) into a reactor containing an aqueous initiator solution thus, obtaining seed polymer particles and then continuously introducing the remaining pre-emulsion.

The temperature in the reactor of step c1 or c2 is from about 70° C. to about 90° C., preferably about 80° C.

The latex obtained by the above described emulsion polymerization process exhibits a colloidal dispersion of polymer particles having a matrix structure, within which the dibenzoylmethane UV-A screening agent or the p-methoxycinnamate UV-B screening agent is homogeneously distributed over the whole volume of the particles.

A latex containing polymer particles having a reservoir structure can be prepared by a two step emulsion polymerization process having a first step polymerization to obtain the core polymer particles and a second step polymerization to obtain polymer particles having at least one shell surrounding the core.

The first polymerization step can be carried out as described above in steps a), b), c1) and c2).

The second polymerization step includes another emulsion polymerization that is carried out according to steps b), c1) and c2) in the presence of the latex prepared in the first polymerization step and in the absence of light screening agents, using the same or different monomers as used in the first step.

In one embodiment of the invention, the second polymerization step includes adding monomers containing carboxylic acid groups such as acrylic acid, methacrylic acid (MAA), monomers bearing hydroxyl groups, such as, e.g., hydroxy-$C_1$–$C_6$-alkyl (meth)acrylate, (HEMA) and acrylamides (AMD).

In another embodiment of the invention, the second polymerization step includes adding monomers containing acrylic esters, such as, e.g., methyl methacrylate (MMA) or isobornyl methacrylate (IBOMA) and fluorinated monomers, such as, e.g., trifluoroethyl methacrylate (TRIFEMA) or perfluoroalkyl 2-ethylacrylate (PF2EA).

The core/shell particles of the present invention can also be prepared by an inverted core/shell polymerization process, in which the shell portion is prepared first, followed by polymerization of the core monomer in the presence of the shell materials.

The weight ratio of the core portion to shell portion is suitably from about 1 to 10.

Suitable emulsifiers are anionic and nonionic surfactants, preferably anionic surfactants.

Conventional anionic surfactants, such as, e.g., alkyl sulfates, alkyl ether sulfates, alkyl succinates, alkyl sulfosuccinates, alkyl phosphates, alkyl ether phosphates, alkyl ether carboxylates, especially their sodium, magnesium, ammonium and mono-, di- and triethanolamine salts can be used. The alkyl groups generally contain from 8 to 18 carbon atoms and may be unsaturated, i.e. $C_{8-18}$-alkenyl groups also come into question as replacements for the alkyl groups in such anionic surfactants.

Suitable anionic surfactants may also be sorbitan derivatives sold under the tradename TWEEN by ICI Americas Incorporated, Wilmington. Preferred are polyoxyethylene-sorbitan-fatty acid esters, such as, e.g., polyoxyethylene(20) sorbitan monolaurate, which is commercialized under the tradename TWEEN 20 (ICI Chemicals).

Another suitable and preferred surfactant is ABEX® 3594 (Rhone-Poulenc) or DOWFAX® 8390 (Dow Chemical).

As used herein the term "initiator solution" refers to an aqueous solution of peroxides, perphosphates, percarbonates, persulfates, organic peroxides, and salts thereof. Preferred is ammonium persulfate.

The polymer particles have a particle size of about 100 nm to about 500 nm, preferably about 100 nm to about 400 nm, more preferably about 250 nm to about 350 nm.

Where convenient the light screening composition of the present invention may further include other conventional UV-A and UV-B screening agents.

The term "conventional UV-B screening agents", i.e., substances having absorption maxima between about 290 and 320 nm, refers to the following UV-B screening agents:

Acrylates, such as 2-ethylhexyl 2-cyano-3,3-diphenylacrylate (octocrylene, PARSOL® 340), ethyl 2-cyano-3,3-diphenylacrylate and the like;

Camphor derivatives, such as methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Organosiloxane compounds containing benzomalonate groups as described in the European Patent Publications EP 0358584 B1, EP 0538431 B1 and the European Publications EP 0709080 A1 and EP 0897716 A2.

Pigments, such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides, such as, e.g., aluminum or zirconium oxides, or by organic coatings, such as, e.g., polyols, methicone, aluminum stearate, alkyl silane. Such coatings are well known in the art.

Imidazole derivatives, such as, e.g., 2-phenylbenzimidazole-5-sulfonic acid and its salts (PARSOL® HS). Salts of 2-phenylbenzimidazole-5-sulfonic acid are, e.g., alkali salts, such as sodium- or potassium salts, ammonium salts, morpholine salts, salts of primary, sec. and tert.amines like monoethanolamine salts, diethanolamine salts and the like.

Salicylate derivatives, such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like;

Triazone derivatives, such as octyl triazone (UVINUL T-150), dioctyl butamido triazone (UVASORB HEB) and the like.

The term "conventional UV-A screening agents", i.e., substances having absorption maxima between about 320 and 400 nm, refers to the following UV-A screening agents:

Dibenzoylmethane derivatives, such as 4-tert. butyl-4'-methoxydibenzoyl-methane (PARSOL® 1789), dimethoxydibenzoyl-methane, isopropyldibenzoyl-methane and the like;

Benzotriazole derivatives, such as 2,2'-methylene-bis-(6-(2H-benzotriazole-2-yl)-4-(1,1,3,3-tetramethylbutyl)-phenol) (TINOSORB M) and the like;

Triazine derivatives, such as 2,4-bis-[4-(2-ethyl-hexyloxy)-2-hydroxy-phenyl]-6-(4-methoxyphenyl)-1,3,5-triazine; available under the tradename TINOSORB S from Ciba Speciality Chemicals Holding Switzerland; and Pigments, such as microparticulated ZnO and the like. The term "micro-particulated" refers to a particle size from about 5 nm to about 200 nm, particularly from about 15 nm to about 100 nm. The ZnO particles may also be coated by metal oxides, such as, e.g., aluminum or zirconium oxides, or by organic coatings, such as, e.g., polyols, methicone, aluminum stearate, alkyl silane. Such coatings are well known in the art.

Suitable organosiloxane compounds are those described in general in the European Patent EP 0538431 B1, namely compounds of the general formula I,

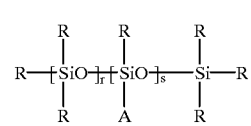

wherein

R signifies $C_{1-6}$-alkyl or phenyl;

A signifies a group of the formula IIa and/or IIb;

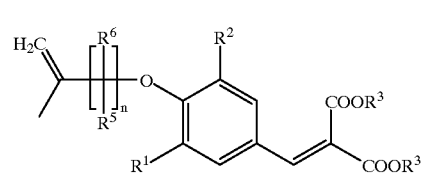

-continued

IIb

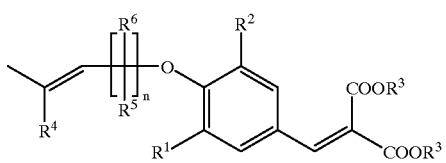

wherein
$R^1$ and $R^2$ each independently signify hydrogen, hydroxy, $C_{1-6}$-alkyl or $C_{1-6}$-alkoxy;
$R^3$ signifies $C_{1-6}$-alkyl;
R signifies hydrogen or $C_{1-6}$-alkyl;
$R^5$ and $R^6$ each independently signify hydrogen or $C_{1-6}$-alkyl;
r has a value of from 0 to 250;
s has a value of from 1 to 20;
r+s has a value of at least 3; and
n has a value from 1 to 6.

The term "$C_{1-6}$-alkyl" refers to groups such as methyl, ethyl, propyl, isopropyl, butyl, sec. butyl, isobutyl, pentyl, and neopentyl.

The term "$C_{1-6}$-alkoxy" refers to the corresponding alkoxy groups.

The residues R are preferably methyl.

The residues $R^1$ and $R^2$ are preferably hydrogen, methoxy or ethoxy, more preferably hydrogen, or one of $R^1$ and $R^2$ is hydrogen and the other is methyl, methoxy or ethoxy.

The residues $R^3$ are preferably methyl or ethyl, more preferably ethyl.

Preferably, $R^4$ is hydrogen or methyl, $R^5$ and $R^6$ are hydrogen and n is 1.

Among the above described organosiloxanes, the following organosiloxane compound of the general formula I described in the European Patent Publication EP 0709080 A1 and hereinafter referred to as "Polysiloxane A" is preferred. Polysiloxane A is a compound of the above formula I, wherein
R signifies methyl;
A signifies a group of the formula IIaa and/or Iibb:

IIaa

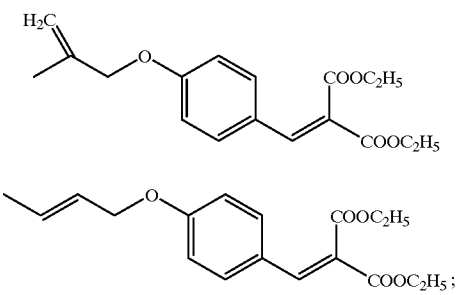

Iibb r is a statistical mean of about 4; and
s is a statistical mean of about 60.

In case A signifies a group of the formula (IIa and IIb) or of the formula (IIaa and Ilbb) respectively, the ratio of polysiloxane units having a chromophore residue A of the formula IIa or IIaa respectively, to those having a chromophore residue A of the formula IIb or IIbb respectively, is not critical.

Other suitable organosilioxane compounds are those described in the European Patent EP 0358584 B1, namely, e.g., compounds of the general formula I wherein R signifies methyl;
A signifies a group of the formula IIc IIc

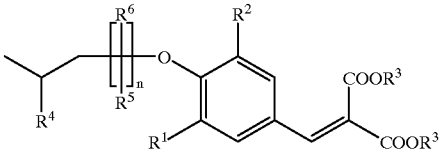

wherein $R^1$–$R^6$ and n are as described above.

The preparation of novel light screening compositions, especially of preparations for skin protection and, respectively, sunscreen preparations for everyday cosmetics is well known to the skilled artisan in this field and comprises incorporating the polymer latex containing the dibenzoylmethane UV-A screening agent or the p-methoxycinnamate UV-B screening agent optionally together with other conventional UV-B screening agents and/or conventional UV-A screening agents as described above in a cosmetic base which is usual for light screening agents.

In a cosmetic composition of the present invention, the polymer latex particles act as carrier for the dibenzoylmethane UV-A screening agent or for the p-methoxycinnamate UV-B screening agent.

The solid content of polymer particles in the latex is suitably from about 10 wt % to about 50 wt %.

The latex contains the dibenzoylmethane UV-A screening agent in an amount of from about 5 wt % to about 30 wt %, preferably from about 5 wt % to about 15 wt %, more preferably from about 6 wt % to about 10 wt %, or the latex contains the p-methoxycinnamate UV-B screening agent in an amount of from about 1 wt % to about 15 wt %, preferably from about 2 wt % to about 8 wt %, more preferably about 5 wt %.

The amount of conventional UV-B screening agents and/or conventional UV-A screening agents is not critical. Suitable amounts include, but are not limited to:
"Polysiloxane A": about 0.5 to about 15 wt %,
PARSOL® 340: about 0.5 to about 10 wt %,
PARSOL® 5000: about 0.5 to about 4 wt %,
PARSOL® HS about 0.5 to about 10 wt %
TINOSORB M: about 0.5 to about 10 wt %,
$TiO_2$: about 0.5 to about 25 wt %,
ZnO: about 0.5 to about 20 wt %.

The light screening compositions of the present invention can be used as cosmetic or pharmaceutical formulations. The term "cosmetic" as used herein denotes topical formulations that are intended for the maintenance, improvement, or restoration of skin and hair. The term "pharmaceutical" as used herein denotes topical formulations that are intended for therapy and prophylaxis of diseases and includes formulations that contain active ingredients that exert a medicinal effect.

The compositions of this invention take the form of a lotion, a gel, a solid stick, an emulsion, e.g., cream, milk, or of a vesicular dispersion of ionic or nonionic amphiphilic lipids, an aerosol, a spray, a foam, a powder, a shampoo, a hair conditioner or lacquer or a make-up, etc. See also, Sunscreens, Development, Evaluation and Regulatory Aspects, eds. Lowe, N. A.; Shaath, M. A.; (Marcel Dekker, Inc.) New York and Basel, 1990.

The usual excipients and auxiliary agents known to the skilled practitioner can be used for the preparation of these forms, e.g., oils, waxes, alcohols, polyols, etc., particularly fatty acids, esters, fatty alcohols, but also ethanol, isopropanol, propylene glycol, glycerine, etc.

The formulations may contain further adjuvants, e.g., further solvents, thickeners, emollients, emulsifiers, humectants, tensides, preservatives, antifoams, fragrances, oils, waxes, lower polyols and monohydric alcohols, propellants, silicones, colourings and pigments, etc.

For protection of the hair, the suitable formulations are shampoos, conditioners, lotions, gels, emulsions, dispersions, lacquers, etc.

The preparation of all these formulations is well known to the skilled artisan in this field.

EXAMPLES

The following examples explain the invention in more detail but do not limit its scope in any manner.

Example 1
Determination of the glass transition temperature

Polymer film was prepared from the latex. The latex was dried and water evaporation gave rise to coalescence of the loaded polymer particles and formation of a film. The glass transition temperature was measured by Differential Scanning Calorimetry (DSC) performed with a DSC Mettler TC11 equipment. Film samples were scanned in sealed aluminum pans in the 30° C./130° C. temperature range, at a heating rate of 10° C./min.

Example 2
Determination of the particle loading

The quantity of dibenzoyl methane UV-A screening agent (loading) incorporated into the polymer particles was determined as follows:

The measurement of PARSOL® 1789 content within the particles (particle loading) was performed using an UV spectrometer working at a wavelength of 357 nm. A known amount of polymer film was introduced in a flask containing tetrahydrofurane (THF). This solvent swelled the latex microparticles and solubilized the encapsulated PARSOL® 1789. The absorption of PARSOL® 1789 was measured and compared with reference solution samples (calibration curve) to determine the actual PARSOL® content in the polymer film. The incorporation rate is defined as the ratio of the PARSOL® 1789 weight incorporated into the polymer particles (measured using UV-technique) over the polymer weight. The encapsulation yield is defined as the ratio of the PARSOL® 1789 weight incorporated into the polymer particles (measured using UV-technique) over the total weight of PARSOL® 1789 introduced.

Example 3
Determination of the photostabilizing effect

The photostabilizing effect was measured by the following method. The amount of latex necessary to get the equivalent of 1 wt % PARSOL® 1789 was calculated from the solid content and the PARSOL® 1789 loading measured, 2 wt % of PARSOL® MCX was added, 30% TWEEN 20 was added and finally completed to 100 wt % with distilled water.

20 mg of the above prepared solution were spread on a glass plate (10 cm$^2$). After a drying time of 30 minutes, three identical samples were irradiated with 10 MED. The samples were then immersed in THF and placed in an ultrasound for 15 minutes. The THF of the three samples together was evaporated and 2 ml of methanol was added to the evaporate. The sample was finally filtered and analyzed by HPLC.

Example 4
Preparation of a latex containing EGDMA

Step a) Solution of PARSOL® 1789

A solution of 58.9 g PARSOL® 1789 was prepared in the blend of the following monomers: 303.9 g MMA, 9.4 g AA, 4.7 g ALMA, 15.7g EGDMA.

Step b) Pre-emulsion

In a polyethylene vessel, 120.1 g of demineralized water were mixed with 5.9 g of an aqueous solution of ABEX® 3594 surfactant (36% solid content) under gentle stirring. The PARSOL® 1789 solution of step a) was continuously added to the aqueous mixture under stirring (8000 rpm) during 30 minutes.

Step c2) Polymerization 3 wt % of the pre-emulsion and a solution of ammonium persulfate were charged into the water containing reactor and heated at 80° C. After 15 minutes, the remaining pre-emulsion was continuously added for 3 hours and 30 minutes at 80° C. The latex was then cured at 80° C. for 120 minutes. The reactor temperature was decreased to 60° C. and a redox system (tert. butyl hydroperoxide/$Na_2S_2O_5$) was fed into the reactor to eliminate residual monomers. The temperature was maintained at 60° C. for 30 minutes. Finally, the latex was cooled to room temperature, filtered through a 50 µm sieve and neutralized to pH 7.3 with NaOH 20 wt %. The solid content of the latex was 46.1 wt %. The particle size of the polymer particles in the latex was about 260 nm. The glass transition temperature was 83.5° C.

The PARSOL® 1789 content was 12.9 wt % in the solid part of the latex and 6 wt % in the latex.

Example 5
Preparation of a latex containing IBOMA

Step a) Solution of PARSOL® 1789

A solution of 58.9 g PARSOL® 1789 was prepared in the blend of the following monomers: 249.5 g MMA, 9.7 g AA, 9.7 g ALMA, and 64.8 g IBOMA.

Step b) Pre-emulsion

In a polyethylene vessel, 132.8 g of demineralized water were mixed with 5.9 g of an aqueous solution of ABEX® 3594 surfactant (36% solid content) under gentle stirring. The PARSOL® 1789 solution of step a) was continuously added to the aqueous mixture under stirring (8000 rpm) during 30 minutes.

Step c2) Polymerization 3 wt % of the pre-emulsion and initiator solution were charged into the water containing reactor and heated at 80° C. After 15 minutes, the remaining pre-emulsion was continuously added for 3 hours and 30 minutes at 80° C. The latex was then cured at 80° C. for 120 minutes. The reactor temperature was decreased to 60° C. and a redox system (tert. butyl hydroperoxide/$Na_2S_2O_5$) was fed into the reactor to eliminate residual monomers. The temperature was maintained at 60° C. for 30 minutes. Finally, the latex was cooled to room temperature, filtered through a 50 µm sieve and neutralized to pH 7.3 with NaOH 20 wt %. The solid content of the latex was 45.2 wt %. The particle size of the polymer particles in the latex was about 303 nm. The glass transition temperature was 90.0° C.

The PARSOL® 1789 content was 13.3 wt % in the solid part of the latex and 6 wt % in the latex.

Example 6

In accordance with Example 4, compositions of modified polymer matrices including functional hydrophilic monomers in the polymerisation step were prepared. The compositions and results are shown in Table I below:

TABLE I

| No. | % MMA | % AA | % ALMA | % EGDMA | hydrophilic monomer % | Tg °C. | Parsol ® 1789 measured % | solids measured % | mean diameter nm |
|---|---|---|---|---|---|---|---|---|---|
| i | 85 | 3 | 1.5 | 5 | HEMA - 5.5 | 83.8 | 13.1 | 46.6 | 275 |
| ii | 88.5 | 3 | 1.5 | 5 | HEMA - 2 | 93.5 | 15 | 43.9 | 262 |
| iii | 88.5 | 3 | 1.5 | 5 | HPMA - 2 | 89.8 | 12.8 | 47.2 | 269 |
| iv | 88.5 | 3 | 1.5 | 5 | AMPS - 2 | 85.6 | 12.4 | 46.2 | 287 |
| v | 88.5 | 3 | 1.5 | 5 | AA - 5 | 113.3 | 12.4 | 44.5 | 264 |
| vi | 88.5 | 3 | 1.5 | 5 | AMD - 1 | 89 | 12.5 | 45.5 | 256 |

Example 7

In accordance with the process of Example 4, but adding a hydrophilic monomer (methacrylic or acrylic acid) after the introduction of 80% of the pre-emulsion, the compositions listed in Table II were prepared:

TABLE II

| No. | % MMA | % AA | % ALMA | % EGDMA | hydrophilic monomer % | Tg °C. | Parsol ® 1789 measured % | solids measured % | mean diameter nm |
|---|---|---|---|---|---|---|---|---|---|
| vii | 86.5 | 3 | 2 | 5 | AA - 3.5 | 79.5 | 14.3 | 45.3 | 336 |
| viii | 86.5 | 3 | 1.5 | 5 | AMA - 3.5 | 86.5 | 12 | 45.9 | 303 |

Example 8

Core-shell nanoparticles were prepared by a two-step emulsion polymerization process. A dispersion of nanoparticles (prepared in accordance with Example 4 using DOWFAX 8390 as the surfactant in the pre-emulsion) is used as a seed to polymerize a polymer shell around the core particles so as to produce a polymer membrane free of screening agent and including hydrophilic monomers. Several blends of monomers were used as summarized in Table III below:

TABLE III

| Blend | MMA | MAA | HEMA | EGDMA | ALMA |
|---|---|---|---|---|---|
| 1 | 41% | 15% | 40% | 2% | 2% |
| 2 | 61% | 10% | 25% | 2% | 2% |
| 3 | 73.5% | 7.5% | 15% | 2% | 2% |
| 4 | 81% | 15% | — | 2% | 2% |

The polymerization process of the shell is performed as described without dilution of the seed latex. However, the same amount of water as the amount of monomers used in the prepartion of the polymer shell is added to the polymerization reactor to form the shell. Therefore, the seed latex and the final core-shell latex display the same solid content. The compositions and the results obtained are given in Table IV:

TABLE IV

| Sample | Seed Latex % SC* | % PARSOL ® 1789 | Monomer Blend No. | Monomer % added | Tg °C. | PARSOL ® 1789 measured (%) | Solid Content measured (%) | Mean diameter (nm) |
|---|---|---|---|---|---|---|---|---|
| ix | 30 | 20 | 1 | 10 | 75.1 / 102.1 | 15.4 | 30.3 | 137 |
| x | 40 | 15 | 2 | 20 | 88.9 / 140.9 | 9.4 | 37.5 | 281 |
| xi | 40 | 15 | 4 | 20 | 95.4 / 137.4 | 9.9 | 38.9 | 367 |
| xii | 50 | 15 | 3 | 20 | 95.8 / 140.4 | 10.6 | 47.2 | 315 |
| xiii | 50 | 20 | 3 | 20 | 87.6 / 135.2 | 13 | 46.4 | 318 |

TABLE IV-continued

| | Seed Latex | | Monomer | | | PARSOL ® 1789 | Solid Content | Mean diameter |
|---|---|---|---|---|---|---|---|---|
| Sample | % SC* | % PARSOL ® 1789 | Blend No. | % added | Tg °C. | measured (%) | measured (%) | (nm) |
| xiv | 50 | 20 | 4 | 20 | 89.9 110.5 | 14 | 46.8 | 314 |

SC* solid content

These latices exhibit two glass transition temperatures, "Tg." The first Tg pertains to the core polymer and the second Tg pertains to the shell polymer.

Example 9

A latex wherein PARSOL® MCX is incorporated into the polymer particles was prepared in accordance with Examples 4 and 5.

The following Examples 10 and 11 refer to sunscreen compositions. The abbreviations and trade names selected have the following significances:

| | |
|---|---|
| ARLACEL P135 | PEG-30 dipolyhydroxystearate sold by ICI; |
| ARLAMOL E | POP-(15)-stearyl alcohol sold by ICI; |
| ARLAMOL HD | Heptamethylnonane sold by ICI; |
| BHT | Butylhydroxytoluol (2,6 di-tert butyl-4-methyl phenol); |
| BRIJ 72 | POE-(2)-stearyl alcohol sold by ICI; |
| BRIJ 721 | POE-(21)-stearyl alcohol sold by ICI; |
| EDETA BD | Disodium EDTA sold by BASF; |
| LANETTE O | Cetearyl alcohol sold by Henkel; |
| PARSOL ® 340 | Octocrylene sold by Roche; |
| PARSOL ® 1789 | 4-tert. Butyl-4'-methoxydibenzoyl-methane sold by Roche; |
| PARSOL ® 5000 | Methyl benzylidene camphor sold by Roche; |
| PARSOL ® HS | 2-Phenylbenzimidazole-5-sulfonic acid sold by Roche; |
| PARSOL ® MCX | 2-Ethylhexyl p-methoxycinnamate sold by Roche; |
| PHENONIP | Phenoxyethanol (and) methylparaben (and) butylparaben (and) ethylparaben (and) propylparaben sold by NIPA; |
| Propylene glycol | 1,2 propanediol sold by BASF; |
| SILBIONE oil 70047 V20 | Cyclomethicone sold by Rhône-Poulenc; |
| SILICONE 1401 Fluid | Cyclomethicone & dimethiconol sold by Dow Corning; |
| SILICONE 5225 C Formulation Aid | Cyclopentasiloxane & dimethicone copolyol sold by Dow Corning; |
| SILICONE DC 344 | Cyclomethicone sold by Dow Corning; |
| SILICONE DC 5200 | Dimethicone copolyol sold by Dow Corning; and |
| UMORDANT P | Na-Lactate & Na-PCA & urea & hydrolyzed vegetable protein & Aspa. |

Example 10

Preparation of a sunscreen O/W lotion containing 23 wt % encapsulated PARSOL® 1789 prepared according to Ex. 4.

| Ingredients | % w/w |
|---|---|
| ARLAMOL E | 5.00 |
| ARLAMOL HD | 5.00 |
| BRIJ 72 | 3.00 |
| BRIJ 721 | 2.00 |
| ARLACEL P135 | 0.50 |
| LANETTE O | 5.00 |
| Stearic Acid | 1.50 |
| SILBIONE Oil 70047 V20 | 1.00 |
| BHT | 0.10 |
| PHENONIP | 0.60 |
| Deionized Water qsp to | 100.00 |
| Xanthan Gum 1% solution | 6.00 |
| Propylene Glycol | 4.00 |
| UMORDANT P | 1.00 |
| PARSOL ® 1789 encapsulated | 23.00 |
| PARSOL ® MCX | 5.00 |

The organic phase containing the UV-filters was heated to 75° C., then the pre-heated aqueous phase (75° C.) was added while stirring. The resulting emulsion was cooled to ambient temperature.

Example 11

Preparation of a sunscreen O/W lotion containing 23 wt % encapsulated PARSOL® 1789 prepared according to Ex. 4.

| Ingredients | % w/w |
|---|---|
| SILICONE 1401 Substantivity Aid Fluid | 10.00 |
| SILICONE 3225C Formulation Aid | 10.00 |
| SILICONE DC 344 | 10.00 |
| SILICONE DC 5200 | 2.00 |
| EDETA BD | 0.10 |
| PHENONIP | 0.60 |
| PARSOL ® HS | 3.00 |
| Glycerol | 5.00 |
| Deionized Water qsp to | 100.00 |
| PARSOL ® 1789 encapsulated | 23.00 |
| Sodium Hydroxyde 10% qsp | pH 7 |

The organic phase containing the UV-filters was heated to 75° C., then the pre-heated aqueous phase (75° C.) was added while stirring. The resulting emulsion was cooled to ambient temperature.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

What is claimed is:

1. A photostable cosmetic or pharmaceutical light screening composition comprising a dibenzoylmethane UV-A screening agent and a p-methoxycinnamate UV-B screening agent wherein one of the UV-A screening agent or the UV-B screening agent is incorporated into a polymer latex.

2. A light screening composition according to claim 1 comprising about 0.5 wt % to about 5 wt % of a dibenzoylmethane UV-A screening agent incorporated into a polymer latex and about 1 wt % to about 15 wt % of a p-methoxycinnamate UV-B screening agent.

3. A light screening composition according to claim 1 comprising about 1 wt % to about 15 wt % of a p-methoxycinnamate UV-B screening agent incorporated into a polymer latex and about 0.5 wt % to about 5 wt % of a dibenzoylmethane UV-A screening agent.

4. A light screening composition according to claim 1 wherein the dibenzoyl-methane UV-A screening agent is 4-tert. butyl-4'-methoxydibenzoyl-methane.

5. A light screening composition according to claim 1 wherein the p-methoxycinnamate UV-B screening agent is 2-ethylhexyl p-methoxycinnamate.

6. A light screening composition according to claim 2 wherein the polymer latex is a stable colloidal dispersion of polymer particles in an aqueous or an aqueous-based phase, including polymers and/or copolymers of unifunctional monomers and/or multifunctional monomers.

7. A light screening composition according to claim 3 wherein the polymer latex is a stable colloidal dispersion of polymer particles in an aqueous or an aqueous-based phase, including polymers and/or copolymers of unifunctional monomers and/or multifunctional monomers.

8. A light screening composition according to claim 6 wherein the unifunctional monomer is selected from the group consisting of $C_1$–$C_6$-alkyl (meth)acrylate, acrylic acid, methacrylic acid, styrene, ethylene, propylene, butylene, butadiene, isoprene, isobornyl methacrylate, trifluoroethyl methacrylate, and perfluoralkyl 2-ethylacrylate.

9. A light screening composition according to claim 7 wherein the unifunctional monomer is selected from the group consisting of $C_1$–$C_6$-alkyl (meth)acrylate, acrylic acid, methacrylic acid, styrene, ethylene, propylene, butylene, butadiene, isoprene, isobornyl methacrylate, trifluoroethyl methacrylate, and perfluoralkyl 2-ethylacrylate.

10. A light screening composition according to claim 6 wherein the multifunctional monomer is selected from the group consisting of allyl methacrylate (ALMA) and ethyleneglycol dimethacrylate (EGDMA).

11. A light screening composition according to claim 7 wherein the multifunctional monomer is selected from the group consisting of allyl methacrylate (ALMA) and ethyleneglycol dimethacrylate (EGDMA).

12. A light screening composition according to claim 6 wherein the polymer particles have a glass transition temperature between about 50° C. and about 100° C.

13. A light screening composition according to claim 7 wherein the polymer particles have a glass transition temperature between about 50° C. and about 100° C.

14. A light screening composition according to claim 2 wherein the polymer latex is a stable colloidal dispersion of copolymer particles of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA).

15. A light screening composition according to claim 3 wherein the polymer latex is a stable colloidal dispersion of copolymer particles of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA).

16. A light screening composition according to claim 6 wherein the polymer particles have a matrix structure within which the dibenzoylmethane UV-A screening agent or the p-methoxycinnamate UV-B screening agent is homogeneously distributed over the whole volume of the particles.

17. A light screening composition according to claim 7 wherein the polymer particles have a matrix structure within which the dibenzoylmethane UV-A screening agent or the p-methoxycinnamate UV-B screening agent is homogeneously distributed over the whole volume of the particles.

18. A light screening composition according to claim 6 wherein the polymer particles have a polymer core surrounded by a polymer shell and the core contains the dibenzoylmethane UV-A screening agent or the methoxycinnamate UV-B screening agent.

19. A light screening composition according to claim 7 wherein the polymer particles have a polymer core surrounded by a polymer shell and the core contains the dibenzoylmethane UV-A screening agent or the methoxycinnamate UV-B screening agent.

20. A light screening composition according to claim 18 wherein the core and the shell portions of the core/shell polymer particles have the same chemical composition with regard to the monomers used.

21. A light screening composition according to claim 19 wherein the core and the shell portions of the core/shell polymer particles have the same chemical composition with regard to the monomers used.

22. A light screening composition according to claim 18 wherein the core and shell portions of the core/shell particles differ in their chemical composition.

23. A light screening composition according to claim 19 wherein the core and shell portions of the core/shell particles differ in their chemical composition.

24. A light screening composition according to claim 22 wherein
 a) the core consists of a polymer and/or a copolymer of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA) and
 b) the shell consists of hydrophilic polymer or fluorinated polymer chains.

25. A light screening composition according to claim 23 wherein
 a) the core consists of a polymer and/or a copolymer of methyl methacrylate (MMA) and acrylic acid (AA) crosslinked with allyl methacrylate (ALMA) and ethyleneglycol dimethacrylate (EGDMA) or containing isobornyl methacrylate (IBOMA) crosslinked with allyl methacrylate (ALMA) and
 b) the shell consists of hydrophilic polymer or fluorinated polymer chains.

26. A method of screening light from human skin or hair comprising administering a light screening amount of a light screening composition of claim 1.

27. A process for preparing a light screening composition comprising polymer latex wherein the polymer particles have a matrix structure, within which a dibenzoylmethane UV-A screening agent or a p-methoxycinnamate UV-B screening agent is homogeneously distributed over the whole volume of the particles, which process consists of
 a) dissolving the dibenzoylmethane UV-A screening agent or the p-methoxy-cinnamate UV-B screening agent in a blend of monomers;
 b) pre-emulsifying the solution of step a) in an aqueous solution containing an emulsifier; and c1) continuously introducing the pre-emulsion of step b) into a reactor containing an aqueous initiator solution or c2) introducing a small amount of the pre-emulsion of step b) into a reactor containing an aqueous initiator solution thus, obtaining seed polymer particles and then continuously introducing the remaining pre-emulsion.

28. A process for preparing a light screening composition comprising polymer latex wherein the polymer particles have a polymer core surrounded by a polymer shell which process comprises a first step polymerization to obtain the core polymer particles and a second step polymerization to obtain polymer particles having at least one shell surrounding the core.

29. A method of photostabilizing mixtures of a dibenzoylmethane UV-A screening agent and a p-methoxycinnamate UV-B screening agent in a light screening composition which method comprises incorporating one of said light screening agents into a polymer latex.

* * * * *

UNITED STATES PATENT AND TRADEMARK OFFICE
CERTIFICATE OF CORRECTION

PATENT NO.    : 6,338,838 B1                                              Page 1 of 1
DATED         : January 15, 2002
INVENTOR(S)   : Guy Berset et al.

It is certified that error appears in the above-identified patent and that said Letters Patent is hereby corrected as shown below:

<u>Title page,</u>
Item [56], References Cited, please insert:

-- English translation of claim 1 of FR 2 687 914
Derwent English language abstract of DE 43 36 407
Derwent English language abstract of FR 2 755 856 --;

<u>Column 16,</u>
Line 57, after "comprising" please insert -- a --;

<u>Column 17,</u>
Line 9, after "comprising" please insert -- a --.

Signed and Sealed this

Tenth Day of September, 2002

Attest:

Attesting Officer

JAMES E. ROGAN
Director of the United States Patent and Trademark Office